United States Patent
Barberich et al.

(10) Patent No.: US 7,030,142 B1
(45) Date of Patent: Apr. 18, 2006

(54) METHODS FOR THE TREATMENT OF NEUROLEPTIC AND RELATED DISORDERS USING ZIPRASIDONE METABOLITES

(75) Inventors: Timothy J. Barberich, Concord, MA (US); Paul D. Rubin, Sudbury, MA (US); William E. Yelle, Littleton, MA (US)

(73) Assignee: Sepracor Inc., Marlborough, MA (US)

( * ) Notice: Subject to any disclaimer, the term of this patent is extended or adjusted under 35 U.S.C. 154(b) by 697 days.

(21) Appl. No.: 09/527,844

(22) Filed: Mar. 17, 2000

Related U.S. Application Data

(60) Provisional application No. 60/127,939, filed on Apr. 6, 1999.

(51) Int. Cl.
  *A01N 43/60* (2006.01)
  *A61K 31/495* (2006.01)
(52) U.S. Cl. .................. 514/340; 514/340; 514/254.02
(58) Field of Classification Search ................. 514/340, 514/254.02
  See application file for complete search history.

(56) References Cited

U.S. PATENT DOCUMENTS

| | | | |
|---|---|---|---|
| 4,411,901 A | 10/1983 | Temple, Jr. et al. | 424/250 |
| 4,590,196 A | 5/1986 | Smith et al. | 514/253 |
| 4,831,031 A * | 5/1989 | Lowe, III et al. | |
| 5,312,925 A * | 5/1994 | Allen et al. | |

FOREIGN PATENT DOCUMENTS

| | | |
|---|---|---|
| EP | EP 0 790 236 A1 | 8/1997 |
| WO | WO 93/16073 | 8/1993 |

OTHER PUBLICATIONS

Geodon (Ziprasidone HCI), Pfizer Inc.*
Prakash et al. Metabolism and Excretion of a New Antipsychotic Drug, Ziprasidone, in Humans, Drug Metabolism and Disposition, vol. 25, No. 7, 863-871 (1997).*
Davis et al., Ziprasidone, abstract, 1997: 593623 CAPLUS, 1997.*
Parkash et al., Metabolism and Excretion of a New Antipsychotic Drug, ziprasidone, in humans: Drug Metabolism and Disposition vol. 25, No. 7, 1997.*
J.P. Yevich et al., "Synthesis and Biological Evaluation of 1-(1,2-Benzisothiazol-3-YL)-and (1,2-Benzisoxazol-3-YL) Piperazine Derivatives as Potential Antipsychotic Agents," *Journal of Medicinal Chemistry*, U.S. American Chemical Society, vol. 29, No. 3, Mar. 1, 1986, pp. 359-369.
Chandra Prakash, et al, "Metabolism and Excretion of the Novel Antipsychotic Drug Ziprasidone in Rats After Oral Administration of a Mixture of $^{14}$C- And $^{3}$H-Labeled Ziprasidone", Drug Metabolism and Disposition, vol. 25, pp. 206-218.
Chandra Prakash, et al., "Metabolism and Excretion of a New Antipsychotic Drug, Ziprasidone in Humans", Drug Metabolism and Disposition, vol. 25, pp. 863-871.

* cited by examiner

*Primary Examiner*—Sreeni Padmanabhan
*Assistant Examiner*—Shahnam Sharareh
(74) *Attorney, Agent, or Firm*—Jones Day

(57) ABSTRACT

The invention relates to novel methods using, and pharmaceutical compositions comprising, ziprasidone metabolites. The methods and compositions of the invention are suitable for the treatment of neuroleptic and related disorders. The invention further encompasses methods of preparing ziprasidone sulfoxide and ziprasidone sulfone.

19 Claims, No Drawings

METHODS FOR THE TREATMENT OF NEUROLEPTIC AND RELATED DISORDERS USING ZIPRASIDONE METABOLITES

This application claims the benefit of Provisional Application No. 60/127,939, filed Apr. 6, 1999.

FIELD OF INVENTION

The invention relates to methods of using, and compositions comprising, ziprasidone metabolites.

BACKGROUND OF THE INVENTION

Ziprasidone, chemically named (5-[2-{4-(1,2-benzisothiazol-3-yl)piperizin-1-yl}ethyl]-6-chlorooxindole)hydrochloride hydrate, is a substituted benzisothiazolylpiperazine. The free base of ziprasidone has the following structure:

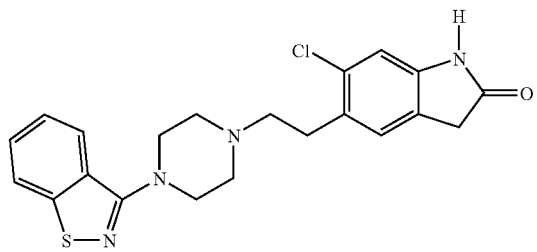

Ziprasidone and some of its uses are described by U.S. Pat. Nos. 4,831,031 and 5,312,925.

Like clozapine and risperidone, ziprasidone is a highly potent and selective 5-HT$_2$ receptor and dopamine D$_2$ receptor antagonist. Seeger, T. F. et al., *J. Pharmacol. Exp. Ther.*, 275(1):101–113 (1995). Ziprasidone is characterized as an antipsychotic, but may also have anxiolytic and antidepressant effects due to its ability to inhibit serotonin and noradrenaline reuptake. Davis, R. and Markham, A., *CNS Drugs*, 8(2):154–159 (1997). The therapeutic potential of ziprasidone may also be enhanced by its high affinity for the 5-HT$_{1A}$, 5-HT$_{1D}$, 5-HT$_{2C}$ receptor subtypes. Seeger, T. F. et al., *J. Pharmacol. Exp. Ther.*, 275(1):101–113 (1995).

The metabolism of ziprasidone is complex. When administered orally to healthy humans, the drug is extensively metabolized by at least four major pathways: 1) N-dealkylation of the ethyl side chain attached to the piperazinyl nitrogen; 2) oxidation at sulfur resulting in the formation of sulfoxide or sulfone; 3) reductive cleavage of the bensisothiazole moiety; and 4) hydration of the C=N bond and subsequent sulfur oxidation or N-dearylation of the benzisothiazole moiety. Prakash, C. et al., *Drug Metab. Dispos.*, 25(7):863–872 (1997). At least 12 human metabolites have been identified: ziprasidone sulfoxide (ZIP-SO); ziprasidone sulfone (ZIP-SO$_2$); 3-(piperazine-1-yl)-1,2-benzisothiazole (BITP); BITP sulfoxide; BITP sulfone; 6-chloro-5-(2-piperazin-1-yl-ethyl)-1,3-dihydroindol-2-one; 6-chloro-5-(2-{4-[imino-(2-mercapto-phenyl)methyl]-piperazin-1-yl}ethyl)-1,3-dihydro-indol-2-one; 6-chloro-5-(2-{4-[imino-(2-methylsulfanyl-phenyl)methyl]-piperazin-1-yl} ethyl)-1,3-dihydro-indol-2-one; S-methyl-dihydro-ziprasidone; S-methyl-dihydro-ziprasidone sulfoxide; dihydro-ziprasidone sulfoxide; and (6-chloro-2-oxo-2,3-dihydro-1H-indol-5-yl)acetic acid. Two metabolites, ZIP-SO and ZIP-SO$_2$, both of which are formed by oxidation of the ziprasidone sulfur atom are discussed herein. These metabolites have the following structures:

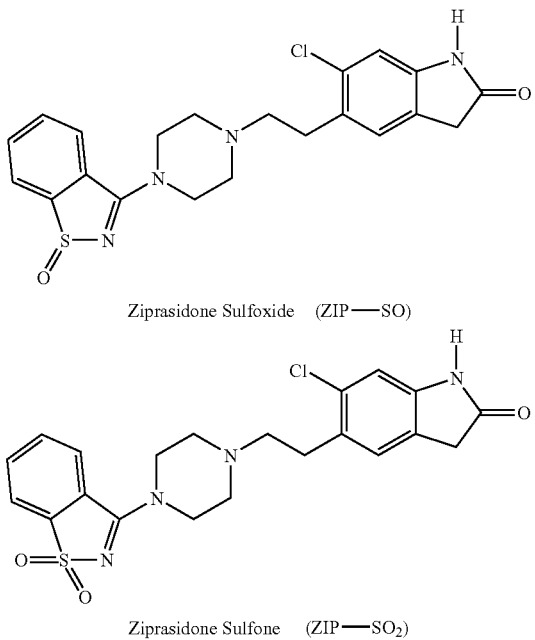

Both ZIP-SO and ZIP-SO$_2$ are minor metabolites, and account for less than about 10% and less than about 3% of ziprasidone metabolites found in human urine, respectively. Prakash, C. et al., *Drug Metab. Dispos.*, 25(7):863–872 (1997). It has been reported that neither metabolite likely contributes to the antipsychotic activity of ziprasidone. Prakash, C. et al., *Drug Metab. Dispos.*, 25(7):863–872 (1997). Indeed, it has been reported that ziprasidone metabolites in general are not active at the D$_2$ and 5-HT$_{2A}$ receptor sites. Ereshefsky, L., *J. Clin. Psych.*, 57(suppl. 11):12–25 (1996).

Ziprasidone offers a number of benefits, but unfortunately many adverse effects are associated with its administration. Examples of adverse affects of ziprasidone include, but are not limited to, nausea, somnolence, asthenia, dizziness, extra-pyramidal symptoms, akathisia, cardiovascular disturbances, male sexual dysfunction, and elevated serum liver enzyme levels. Davis, R. and Markham, A., *CNS Drugs*, 8(2):154–159 (1997). These adverse effects can significantly limit the dose level, frequency, and duration of drug therapy. It is thus desirable to find a compound which possesses advantages of ziprasidone but fewer of its disadvantages.

3. SUMMARY OF THE INVENTION

This invention relates to novel methods using, and compositions comprising, ziprasidone metabolites, preferably, ziprasidone sulfoxide and ziprasidone sulfone. These metabolites, prior to the present invention, have been reported to have little or no in vivo activity. The present invention encompasses the in vivo use of these metabolites, and their incorporation into pharmaceutical compositions and single unit dosage forms useful in the treatment and prevention of disorders that are ameliorated by the inhibition of serotonin reuptake at 5-HT$_2$ receptors and/or the inhibition of dopamine reuptake at dopamine D$_2$ receptors. Such disorders include psychotic and neuroleptic disorders. In a preferred embodiment, ziprasidone metabolites are used in the treatment or prevention of neuroleptic and related disorders in mammals, including humans.

The compounds and compositions of the invention further allow the treatment and prevention of the diseases and disorders while reducing or avoiding adverse effects associated with the administration of ziprasidone.

3.1 DEFINITIONS

As used herein, the term "patient" refers to a mammal, particularly a human.

As used herein, the term "ziprasidone metabolite" means a compound that is a product of the metabolism of ziprasidone in a human. Ziprasidone metabolites include, but are not limited to: ziprasidone sulfoxide (ZIP-SO); ziprasidone sulfone (ZIP-SO$_2$); 3-(piperazine-1-yl)-1,2-benzisothiazole (BITP); BITP sulfoxide; BITP sulfone; 6-chloro-5-(2-piperazin-1-yl-ethyl)-1,3-dihydro-indol-2-one; 6-chloro-5-(2-{4-[imino-(2-mercaptophenyl)methyl]-piperazin-1-yl} ethyl)-1,3-dihydro-indol-2-one; 6-chloro-5-(2-{4-[imino-(2-methylsulfanyl-phenyl)methyl]-piperazin-1-yl} ethyl)-1,3-dihydro-indol-2-one; S-methyl-dihydro-ziprasidone; S-methyl-dihydro-ziprasidone sulfoxide; dihydro-ziprasidone sulfoxide; and (6-chloro-2-oxo-2,3-dihydro-1H-indol-5-yl)acetic acid. Preferred ziprasidone metabolites include ZIP-SO and ZIP-SO$_2$.

As used herein, the term "pharmaceutically acceptable salts" refers to salts prepared from pharmaceutically acceptable non-toxic acids, including inorganic acids and organic acids. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Preferred non-toxic acids include hydrochloric, hydrobromic, phosphoric, sulfuric, and methanesulfonic acids. Examples of preferred salts thus include hydrochloride and mesylate salts.

As used herein, the term "a method of treating disorders ameliorated by the inhibition of serotonin reuptake at 5-HT$_2$ receptors and/or the inhibition of dopamine reuptake at dopamine D$_2$ receptors in a patient" means relief from symptoms of disease states associated with abnormal serotonin and/or dopamine levels; such symptoms are reduced or relieved by way of inhibition of serotonin reuptake at 5-HT$_2$ receptors and/or the inhibition of dopamine reuptake at dopamine D$_2$ receptors in a patient. Disorders treated by inhibition of serotonin reuptake at 5-HT$_2$ receptors and/or the inhibition of dopamine reuptake at dopamine D$_2$ receptors in a patient include, but are not limited to, neuroleptic disorders, migraines, acute intermittent porphyria, intractable hiccups, Parkinson's disease and epilepsy.

As used herein, the term "psychosis" means a mental or behavioral disorder, with or without organic damage, causing gross distortion or disorganization of a person's mental capacity, affective response, capacity to recognize reality, communicate, or relate to others such that his or her capacity to cope with the ordinary demands of everyday life is diminished. Psychosis includes, but is not limited to, hallucinations, paranoia, affective psychosis (manic psychosis), alcoholic psychoses, arteriosclerotic psychosis, amnestic psychosis, bipolar psychosis (manic-depressive psychosis), Cheyne-Stokes psychosis, climacteric psychosis, depressive psychosis, drug psychosis, dysmnesic psychosis, hysterical psychosis, infection-exhaustion psychosis, Korsakoff's psychosis, postinfectious psychosis, postpartum psychosis, posttraumatic psychosis, senile psychosis, situational psychosis, toxic psychosis, traumatic psychosis, Windigo psychosis, schizo-affective psychosis, schizophrenia and related disorders. *Diagnostic and Statistical Manual of Mental Disorders*, 4$^{th}$ *Ed.*, American Psychiatric Association (1997) (DSM-IV™).

As used herein, the term "affective disorder" means a disorder selected from the group including, but not limited to, depression, attention deficit disorder, attention deficit disorder with hyperactivity, and bipolar and manic conditions. The terms "attention deficit disorder" (ADD) and "attention deficit disorder with hyperactivity" (ADDH), or attention deficit/hyperactivity disorder (AD/HD), are used herein in accordance with the accepted meanings as found in the *Diagnostic and Statistical Manual of Mental Disorders*, 4$^{th}$ *Ed.*, American Psychiatric Association (1997) (DSM-IV™), and *Diagnostic and Statistical Manual of Mental Disorders*, 3$^{rd}$ *Ed.*, American Psychiatric Association (1981) (DSM-III™).

As used herein, the term "a method of treating or preventing depression" means relief from the symptoms of depression which include, but are not limited to, changes in mood, feelings of intense sadness, despair, mental slowing, loss of concentration, pessimistic worry, agitation, and self-deprecation. Physical changes may also be relieved, including insomnia, anorexia, weight loss, decreased energy and libido, and abnormal hormonal circadian rhythms.

As used herein, the term "anxiety" is consistent with accepted meaning in the art. See, e.g., DSM-IV™. Anxiety includes, but is not limited to, anxiety attacks, free-floating anxiety, noetic anxiety, separation anxiety, and situation anxiety. The terms "methods of treating or preventing" when used in connection with these disorders means amelioration, prevention or relief from the symptoms and/or effects associated with these disorders.

As used herein, the term "adverse effects of ziprasidone" means an effect selected from the group including, but not limited to, nausea, somnolence, asthenia, dizziness, motor disturbances (extrapyramidal symptoms), akathisia, cardiovascular disturbances (postural hypotension and tachycardia), respiratory disorder (described as coryzal symptoms, not nasal stuffiness), headache, dyspepsia, male sexual dysfunction, and elevated serum liver enzyme levels.

4. DETAILED DESCRIPTION OF THE INVENTION

The invention relates to methods of treating neuroleptic and related disorders using ziprasidone metabolites, and using ZIP-SO and ZIP-SO$_2$ in particular. Until now, ZIP-SO and ZIP-SO$_2$ were believed to possess little or no pharmacological activity. This invention further relates to solid and liquid pharmaceutical compositions and single unit dosage forms comprising a ziprasidone metabolite, such as ZIP-SO and ZIP-SO$_2$, as well as to methods of making ZIP-SO and ZIP-SO$_2$.

The methods and compositions of the invention can be used in the treatment and prevention of disorders described herein while avoiding or reducing drug—drug interactions and other adverse effects associated with agents known for the treatment of such disorders, including ziprasidone. The ziprasidone metabolites of the invention may further provide an overall improved therapeutic index over ziprasidone.

A first embodiment of the invention encompasses a method of treating or preventing disorders ameliorated by the inhibition of serotonin reuptake at 5-HT$_2$ receptors and/or the inhibition of dopamine reuptake at dopamine D$_2$ receptors in a patient. The 5-HT$_2$ and D$_2$ receptors may be centrally (i.e., in the central nervous system) or peripherally located. This method comprises administering to a patient in need of such treatment or prevention a therapeutically effective amount of a ziprasidone metabolite, or a pharmaceutically acceptable salt, solvate, hydrate, or clathrate thereof. Preferred ziprasidone metabolites include ZIP-SO and ZIP-SO$_2$. Disorders ameliorated by the inhibition of serotonin reuptake at 5-HT$_2$ receptors and/or the inhibition of dopamine reuptake at dopamine D$_2$ receptors include, but are not limited to, neuroleptic disorders, pain, migraines, acute intermittent porphyria, intractable hiccups, Parkinson's disease and epilepsy. Neuroleptic disorders include, but are not limited to, psychosis, affective disorders, and anxiety.

A preferred embodiment of the invention thus encompasses a method of treating or preventing psychosis in a patient which comprises administering to a patient in need of such treatment or prevention a therapeutically effective amount of a ziprasidone metabolite, or a pharmaceutically acceptable salt, solvate, hydrate, or clathrate thereof. This embodiment encompasses methods of treating and preventing schizophrenia, schizo-affective psychosis, hallucinations, paranoia, affective psychosis (manic psychosis), alcoholic psychoses, arteriosclerotic psychosis, amnestic psychosis, bipolar psychosis (manic-depressive psychosis), Cheyne-Stokes psychosis, climacteric psychosis, depressive psychosis, drug psychosis, dysmnesic psychosis, hysterical psychosis, infection-exhaustion psychosis, Korsakoff's psychosis, postinfectious psychosis, postpartum psychosis, posttraumatic psychosis, senile psychosis, situational psychosis, toxic psychosis, traumatic psychosis, and Windigo psychosis.

Another preferred embodiment of the invention encompasses a method of treating or preventing an affective disorder in a patient which comprises administering to a patient in need of such treatment or prevention a therapeutically effective amount of a ziprasidone metabolite, or a pharmaceutically acceptable salt, solvate, hydrate, or clathrate thereof. This embodiment encompasses methods of treating and preventing depression, attention deficit disorder, attention deficit disorder with hyperactivity, combativeness, explosive hyperexcitable behavior, and bipolar and manic conditions.

A further preferred embodiment of the invention encompasses a method of treating and preventing anxiety in a patient which comprises administering to a patient in need of such treatment or prevention a therapeutically effective amount of a ziprasidone metabolite, or a pharmaceutically acceptable salt, solvate, hydrate, or clathrate thereof. This embodiment encompasses methods of treating and preventing anxiety attacks, free-floating anxiety, noetic anxiety, separation anxiety, and situation anxiety.

Another embodiment of the invention encompasses a method for treating and preventing pain in a patient which comprises administering to a patient in need of such treatment or prevention a therapeutically effective amount of a ziprasidone metabolite, or a pharmaceutically acceptable salt, solvate, hydrate, or clathrate thereof.

In a particular method encompassed by this embodiment, a ziprasidone metabolite, or a pharmaceutically acceptable salt, solvate, hydrate, or clathrate thereof, is adjunctively administered with at least one additional therapeutic agent. Examples of additional therapeutic agents include, but are not limited to: tricyclic antidepressants such as desipramine, imipramine, amytriptiline, and nortriptile; anticonvulsants such as carbamazepine and valproate; serotonin reuptake inhibitors such as fluoxetine, paraoxetine, sertraline, and methysergide; mixed serotonin-norepinephrine reuptake inhibitors such as venlafaxine and duloxetine; serotonin receptor agonists; cholinergenic (muscarinic and nicotinic) analgesics such as ketoprofen, aspirin, acetaminophen, indomethacin, ketorolac, and methotrimeprazine; adrenergic agents; neurokinin antagonists; xanthine oxidase inhibitors such as allopurinol; and pharmaceutically acceptable salts and solvates thereof.

A second embodiment of the invention encompasses pharmaceutical compositions comprising a ziprasidone metabolite, or a pharmaceutically acceptable salt, solvate, hydrate, or clathrate thereof. Preferred ziprasidone metabolites include ZIP-SO and ZIP-SO$_2$. This embodiment further encompasses individual dosage forms of ziprasidone metabolites, or pharmaceutically acceptable salts, solvates, hydrates, or clathrates thereof.

Individual dosage forms of the invention may be suitable for oral, mucosal (including rectal, nasal, or vaginal), parenteral (including subcutaneous, intramuscular, bolus injection, intraarterial, or intravenous), sublingual, transdermal, buccal, or topical administration.

A particular pharmaceutical composition encompassed by this embodiment comprises a ziprasidone metabolite, or a pharmaceutically acceptable salt, solvate, hydrate, or clathrate thereof, and at least one additional therapeutic agent. Examples of additional therapeutic agents include, but are not limited to: tricyclic antidepressants such as desipramine, imipramine, amytriptiline, and nortriptile; anticonvulsants such as carbamazepine and valproate; serotonin reuptake inhibitors such as fluoxetine, paraoxetine, sertraline, and methysergide; mixed serotonin-norepinephrine reuptake inhibitors such as venlafaxine and duloxetine; serotonin receptor agonists; cholinergenic (muscarinic and nicotinic) analgesics such as ketoprofen, aspirin, acetaminophen, indomethacin, ketorolac, and methotrimeprazine; adrenergic agents; neurokinin antagonists; xanthine oxidase inhibitors such as allopurinol; and pharmaceutically acceptable salts and solvates thereof.

A third embodiment of the invention encompasses methods of preparing ZIP-SO and ZIP-SO$_2$. These methods comprise treating ziprasidone with at least one oxidizing agent. Preferably, the oxidizing agent is selected form the group consisting of hydrogen peroxide; sodium periodate; alkylperoxides; alkylhydroperoxides; hypochlorites, such as sodium hypochlorite and calcium hypochlorite; dioxiranes; nitric acid and a group VIII, IB and IIB transition metal catalyst; molecular oxygen or air and a lanthanide or transition metal catalyst; acyl nitrites; sodium perborate; and peracids.

4.1. SYNTHESIS AND PREPARATION

Ziprasidone sulfoxide (ZIP-SO) and ziprasidone sulfone (ZIP-SO$_2$) are readily prepared from ziprasidone using oxidation methods known to those skilled in the art. A syntheses of ziprasidone are described in U.S. Pat. Nos. 4,831,031; 5,206,366; 5,338,846; and 5,359,068, the disclosure of which is hereby incorporated by reference.

In general, sulfoxides are formed by oxidation of thioalkyl groups using one mole equivalent of an oxidizing agent. Sulfoxides can be further oxidized to sulfones by using a second mole of an oxidizing agent. Preferably, the oxidizing agent is hydrogen peroxide; sodium periodate; alkylperoxides; alkylhydroperoxides; hypochlorites, such as sodium hypochlorite and calcium hypochlorite; dioxiranes; nitric acid and a gold tetrachloride catalyst; potassium permanganate; sodium perborate; potassium hydrogen persulfate; molecular oxygen and a ceric ammonium nitrate catalyst; acyl nitrites; sodium perborate; and peracids. March, J., *Advanced Organic Chemistry.* 4$^{th}$ *Edition*, John Wiley & Sons, pp. 1201–1203 (1992). When sufficient amounts of oxidizing agent are present, thioalkyl groups can be converted directly to sulfones without isolation of sulfoxides. If necessary, the nitrogen of the benzisothialolyl ring can be protected using suitable methods known to those skilled in the art; an example is the reaction with anhydride to yield the corresponding amide, which can be removed after oxidation of sulfur. See, e.g., March, *J. Advanced Organic Chemistry*, 4$^{th}$ *Edition* p. 401 and 418–419 (1985). Suitable solvents include acetonitrile, methylene chloride, benzene, toluene, N-methylpyrrolidinone, dimethylformamide, ethanol, methanol, isopropanol, propanol, butanol, isobutanol, tertbutyl alcohol, dimethylsulfoxide, diethyl ether, tetrahydrofuran, acetone, and mixtures thereof, including aqueous mixtures where appropriate.

4.2. PHARMACERTICAL COMPOSITIONS AND METHOD OF UDE

The active compounds of the invention (i.e., ziprasidone metabolites) are antipsychotic and antineuroleptic agents, and may thus be used in the treatment or prevention of a wide range of diseases and conditions. The magnitude of a prophylactic or therapeutic dose of a particular active ingredient of the invention in the acute or chronic management of a disease or condition will vary, however, with the nature and severity of the disease or condition, and the route by which the active ingredient is administered. The dose, and perhaps the dose frequency, will also vary according to the age, body weight, and response of the individual patient. Suitable dosing regimens can be readily selected by those skilled in the art with due consideration of such factors. In general, the recommended daily dose range for the conditions described herein lie within the range of from about 1 mg to about 1000 mg per day, given as a single once-a-day dose in the morning but preferably as divided doses throughout the day taken with food. More preferably, the daily dose is administered twice daily in equally divided doses. Preferably, a daily dose range should be from about 5 mg to about 500 mg per day, more preferably, between about 10 mg and about 200 mg per day. In managing the patient, the therapy should be initiated at a lower dose, perhaps about 1 mg to about 25 mg, and increased if necessary up to about 200 mg to about 1000 mg per day as either a single dose or divided doses, depending on the patient's global response.

It may be necessary to use dosages of the active ingredient outside the ranges disclosed herein in some cases, as will be apparent to those of ordinary skill in the art. Because elimination of ziprasidone metabolites from the bloodstream is dependant on renal and liver function, it is recommended that the total daily dose be reduced by at least 50% in patients with moderate hepatic impairment, and that it be reduced by 25% in patients with mild to moderate renal impairment. For patients undergoing hemodialysis, it is recommended that the total daily dose be reduced by 5% and that the dose be withheld until the dialysis treatment is completed. Furthermore, it is noted that the clinician or treating physician will know how and when to interrupt, adjust, or terminate therapy in conjunction with individual patient response.

The phrase "therapeutically effective amount," as used herein with respect to the treatment or prevention of disorders ameliorated by the inhibition of serotonin reuptake at 5-HT$_2$ receptors and/or the inhibition of dopamine reuptake at dopamine D$_2$ receptors, such as neuroleptic disorders, encompasses the above described dosage amounts and dose frequency schedules. Different therapeutically effective amounts may be applicable for different diseases and conditions, as will be readily known by those of ordinary skill in the art. Similarly, amounts sufficient to treat or prevent such disorders, but insufficient to cause, or sufficient to reduce, adverse effects associated with ziprasidone, are also encompassed by the above described dosage amounts and dose frequency schedules.

Any suitable route of administration may be employed for providing the patient with an effective dosage of a ziprasidone metabolite. For example, oral, mucosal (including rectal), parenteral (including subcutaneous, intramuscular, bolus injection, and intravenous), sublingual, transdermal, nasal, buccal, and like may be employed. In the acute treatment or management of a disease or condition, it is preferred that the active ingredient be administered orally. In the acute treatment or management of a disease or condition, it is preferred that the active ingredient be administered parenterally.

The pharmaceutical compositions of the invention comprise at least one ziprasidone metabolite, or a pharmaceutically acceptable salt, solvate, hydrate, or clathrate thereof as an active ingredient, and may also contain a pharmaceutically acceptable carrier and optionally other therapeutic ingredients known to those skilled in the art, including the additional therapeutic ingredients listed above. The pharmaceutical compositions may be solid or liquid. Examples of solid compositions include crystalline, non-crystalline (i.e., amorphous), hydrated, and anhydrous compositions. Preferred pharmaceutical compositions are hydrates, including, but not limited to, mesylate dihydrates, mesylate trihydrates, and hydrochloride monohydrates. Such hydrates are described in U.S. Pat. No. 5,312,925, PCT Publication No. WO/97/42190, and PCT Publication No. WO/97/42191, the disclosures of which are each incorporated herein. The pharmaceutical compositions may also be inclusion complexes, such as those described in PCT Publication No. WO 97/41896, the disclosure of which is incorporated herein.

Compositions of the invention are suitable for oral, mucosal (including rectal), parenteral (including subcutaneous, intramuscular, bolus injection, and intravenous), sublingual, transdermal, nasal, or buccal administration, although the most suitable route in any given case will depend on the nature and severity of the condition being treated. The compositions may be conveniently presented in unit dosage form and prepared by any of the methods well known in the part of pharmacy. Dosage forms include tablets, caplets, troches, lozenges, dispersions, suspensions, suppositories, solutions, capsules, soft elastic gelatin capsules, patches, and the like. Preferred dosage forms are suitable for oral administration. Lyophilized dosage forms may be orally administered, or may be reconstituted to provide sterile, liquid dosage forms suitable for parenteral administration to a patient.

In practical use, a ziprasidone metabolite can be combined as the active ingredient in intimate admixture with a pharmaceutically acceptable carrier according to conventional pharmaceutical compounding techniques. The carrier may take a wide variety of forms and comprises a number of components depending on the form of preparation desired for administration. The compositions of the invention include, but are not limited to, suspensions, solutions and elixirs; aerosols; or excipients, including, but not limited to, starches, sugars, microcrystalline cellulose, diluents, granulating agents, lubricants, binders, disintegrating agents, and the like. Preferably, the pharmaceutical composition is in the form of an oral preparation.

Pharmaceutical compositions of the invention suitable for oral administration may be presented as discrete pharmaceutical unit dosage forms, such as capsules, cachets, soft elastic gelatin capsules, tablets, caplets, or aerosols sprays, each containing a predetermined amount of the active ingredients, as a powder or granules, or as a solution or a suspension in an aqueous liquid, a non-aqueous liquid, an oil-in-water emulsion, or a water-in-oil liquid emulsion. Such compositions may be prepared by any method known in the art of pharmacy which comprises the step of bringing an active ingredient into association with a carrier. In general, the compositions are prepared by uniformly and intimately admixing the active ingredients with liquid carriers or finely divided solid carriers or both, and then, if necessary, shaping the product into the desired presentation. Oral solid preparations are preferred over oral liquid preparations. Preferred oral solid preparations are capsules and tablets.

A tablet may be prepared by compression or molding techniques. Compressed tablets may be prepared by compressing in a suitable machine the active ingredient in a free-flowing form, such as powder or granules, optionally mixed with a binder, lubricant, inert diluent, granulating agent, surface active or dispersing agent, or the like. Molded tablets may be made by molding, in a suitable machine, a mixture of the powdered compound moistened with an inert liquid diluent. Preferably, each tablet, cachet, caplet, or capsule contains from about 1 mg to about 1000 mg of ziprasidone metabolite, more preferably from about 5 mg to about 500 mg, and most preferably from about 10 mg to about 200 mg.

Pharmaceutical compositions of the invention may also be formulated as a pharmaceutical composition in a soft elastic gelatin capsule unit dosage form by using conventional methods well known in the art. See, e.g., Ebert, *Pharm. Tech.*, 1(5):44–50 (1977). Soft elastic gelatin capsules have a soft, globular gelatin shell somewhat thicker than that of hard gelatin capsules, wherein a gelatin is plasticized by the addition of plasticizing agent, e.g., glycerin, sorbitol, or a similar polyol. The hardness of the capsule shell may be changed by varying the type of gelatin used and the amounts of plasticizer and water. The soft gelatin shells may contain a preservative, such as methyl- and propylparabens and sorbic acid, to prevent the growth of fungi. The active ingredient may be dissolved or suspended in a liquid vehicle or carrier, such as vegetable or mineral oils, glycols, such as polyethylene glycol and propylene glycol, triglycerides, surfactants, such as polysorbates, or a combination thereof.

A pharmaceutically acceptable excipient used in the compositions and dosage form of the invention may be a binder, a filler, a mixture thereof. A pharmaceutically acceptable excipient may also include a lubricant, a disintegrant, or mixtures thereof. Preferred excipients are lactose, croscarmellose, microcrystalline cellulose, pre-gelatinized starch, and magnesium stearate. One embodiment of the invention encompasses a pharmaceutical composition which is substantially free of all mono- or di-saccharide excipients.

Binders suitable for use in the compositions and dosage forms of the invention include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose or mixtures thereof.

Suitable forms of microcrystalline cellulose include, for example, the materials sold as AVICEL-PH-101, AVICEL-PH-103 and AVICEL-PH-105 (available from FMC Corporation, American Viscose Division, Avicel Sales, Marcus Hook, Pa., U.S.A.). An exemplary suitable binder is a mixture of microcrystalline cellulose and sodium carboxymethyl cellulose sold as AVICEL RC-581 by FMC Corporation.

Fillers suitable for use in the compositions and dosage forms of the invention include, but are not limited to, talc, calcium carbonate (e g, granules or powder), microcrystalline cellulose, powdered cellulose, dextrates, kaolin, mannitol, silicic acid, sorbitol, starch, pre-gelatinized starch, or mixtures thereof.

The binder/filler in pharmaceutical compositions of the invention is typically present in about 50 to about 99 weight percent of the pharmaceutical composition.

Disintegrants are used to cause the tablet to disintegrate when exposed to an aqueous environment. Too much of a disintegrant will produce tablets which may disintegrate in the bottle due to atmospheric moisture; too little may be insufficient for disintegration to occur and may thus alter the rate and extent of release of the drug ingredient(s) from the dosage form. Thus, a sufficient amount of disintegrant that is neither too little nor too much to detrimentally alter the release of the drug ingredient(s) should be used to form dosage forms of ziprasidone metabolite made according to the invention. The amount of disintegrant used varies based upon the type of formulation and mode of administration, and is readily discernible to those of ordinary skill in the art. Typically, about 0.5 to about 15 weight percent of disintegrant, preferably about 1 to about 5 weight percent of disintegrant, may be used in the pharmaceutical composition.

Disintegrants suitable for use in the compositions and dosage forms of the invention include, but are not limited to, agar—agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants suitable for use in the compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, or mixtures thereof. Additional lubricants include, for example, a syloid silica gel (AEROSIL 200, manufactured by W.R. Grace Co. of Baltimore Md.), a coagulated aerosol of synthetic silica (marketed by Deaussa Co. of Plano, Tex.), CAB-O-SIL (a pyrogenic silicon dioxide product sold by Cabot Co. of Boston, Mass.), or mixtures thereof A lubricant may optionally be added, typically in an amount of less than about 1 weight percent of the pharmaceutical composition.

In addition to the common dosage forms set out above, the compounds of the invention may also be administered by controlled release means or delivery devices that are well known to those of ordinary skill in the art, such as those described in U.S. Pat. Nos. 3,845,770; 3,916,899; 3,536, 809; 3,598,123; and 4,008,719, 5,674,533, 5,059,595, 5,591, 767, 5,120,548, 5,073,543, 5,639,476, 5,354,556, and 5,733, 566, the disclosures of which are each incorporated herein by express reference thereto. These pharmaceutical compositions can be used to provide slow or controlled-release of one or more of the active ingredients therein using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable controlled-release formulations known to those of ordinary skill in the art, including those described herein, may be readily selected for use with the pharmaceutical compositions of the invention. Thus, single unit dosage forms suitable for oral administration, such as tablets, capsules, gelcaps, caplets, and the like, that are adapted for controlled-release are encompassed by the invention.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations may include: 1) extended activity of the drug; 2) reduced dosage frequency; 3) increased patient compliance; and 4) a lower peak plasma concentration of the drug. The latter advantage is significant because high peak plasma concentrations of some drugs can cause adverse effects not associated with lower, but still therapeutically effective, plasma concentrations.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

The controlled-release of an active ingredient may be stimulated by various inducers, for example pH, temperature, enzymes, water, or other physiological conditions or compounds. The term "controlled-release component" in the context of the invention is defined herein as a compound or compounds, including, but not limited to, polymers, polymer matrices, gels, permeable membranes, liposomes, microspheres, or the like, or a combination thereof, that facilitates the controlled-release of the active ingredient.

Pharmaceutical compositions of the invention may also be formulated for parenteral administration by injection (subcutaneous, bolus injection, intramuscular, or intravenous), and may be dispensed in a unit dosage form, such as a multidose container or an ampule. Such compositions for parenteral administration may be in the form of suspensions, solutions, emulsions, or the like in aqueous or oily vehicles, and in addition to the active ingredients may contain one or more formulary agents, such as dispersing agents, suspending agents, stabilizing agents, preservatives, and the like.

The invention is further defined by reference to the following examples describing in detail the preparation of the compositions of the invention. It will be apparent to those skilled in the art that many modifications, both to materials and methods, may be practiced without departing from the purpose and interest of this invention.

5. EXAMPLES

5.1. Example 1

Synthesis of Ziprasidone

To a 125 mL round bottom flask equipped with an $N_2$ inlet and condenser are added 0.73 g (3.2 mmol) 5-(2-chloroethyl)-6-chloro-oxindole, 0.70 g (3.2 mmol) N-(1,2-benzisothiazol-3-yl)piperazine, 0.68 g (6.4 mmol) sodium carbonate, 2 mg sodium iodide, and 30 mL methylisobutyl ketone. The reaction is refluxed for 40 hours, cooled, filtered, and evaporated. The residue is chromatographed on silica gel, eluting the by-products with ethyl acetate (1 L) and the product with 4% methanol in ethyl acetate (1.5 L). The product fractions ($R_f$=0.2 in 5% methanol in ethyl acetate) are evaporated, taken up in methylene chloride, and precipitated by addition of ether saturated with HCl; the solid is filtered and washed with ether, dried, and washed with acetone. The latter is done by slurrying the solid with acetone and filtering. Ziprasidone is obtained as a high melting, non-hygroscopic solid product having an expected melting point of 288° C. to 288.5° C.

5.2. Example 2

Synthesis of Ziprasidone Sulfoxide

To a solution of ziprasidone made as described in Example 1 (0.70 g, 1.7 mmol) in acetonitrile is added 30% $H_2O_2$ (1.7 mmol). After stirring for 24 hours at room temperature, the reaction mixture is cooled, filtered, and evaporated. The residue is chromatographed on silica gel, eluting the by-products with ethyl acetate (1 L) and the product with 4% methanol in ethyl acetate (1.5 L). The product fractions are evaporated, taken up in methylene chloride, and precipitated by addition of ether saturated with HCl; the solid is filtered and washed with ether, dried, and washed with acetone.

5.3. Example 3

Synthesis of Ziprasidone Sulfone

To a solution of ziprasidone sulfoxide made as described in Example 2 (0.76 g, 1.7 mmol) in acetonitrile is added 30% $H_2O_2$ (1.7 mmol). After stirring for 24 hours at room temperature, the reaction mixture is cooled, filtered, and evaporated. The residue is chromatographed on silica gel, eluting the by-products with ethyl acetate (1 L) and the product with 4% methanol in ethyl acetate (1.5 L). The product fractions are evaporated, taken up in methylene chloride, and precipitated by addition of ether saturated with HCl; the solid is filtered and washed with ether, dried, and washed with acetone.

Alternatively, ziprasidone sulfone may be obtained by one step oxidation of ziprasidone. To a solution of ziprasidone made as described in Example 1 (0.70 g, 1.7 mmol) in acetonitrile is added 30% $H_2O_2$ (3.4 mmol). After stirring for 24 hours at room temperature, the reaction mixture is cooled, filtered, and evaporated. The residue is chromatographed on silica gel, eluting the by-products with ethyl acetate (1 L) and the product with 4% methanol in ethyl acetate (1.5 L). The product fractions are evaporated, taken up in methylene chloride, and precipitated by addition of ether saturated with HCl; the solid is filtered and washed with ether, dried, and washed with acetone.

5.4. Example 4

5-HT$_2$ Receptor Activity

Receptor selection and amplification technology (R-SAT) is used (Receptor Technologies Inc., Winooski, Vt.) to determine potential agonist and/or antagonist activity of ziprasidone and ziprasidone metabolites on cloned human serotonin 5-HT$_2$ receptor subtypes expressed in NIH 3T3 cells. This assay is a modification of a known assay to determine potential agonist and/or antagonist activity of racemic norcisapride, cisapride and their enantiomers. (Burstein et al, *J. Biol. Chem.*, 270:3141–3146 (1995); and Messier et al., *Pharmacol. Toxicol.*, 76(5):308–311 (1995)).

The assay involves co-expression of a marker enzyme, β-galactosidase, with the serotonin receptor of interest. Ligands stimulate proliferation of cells that express the receptor and, therefore, the marker. Ligand-induced effects can be determined by assay of the marker.

NIH 3T3 cells are incubated, plated, and then transfected using human 5-HT$_2$ serotonin receptors, pSV-β-galactosidase, and salmon sperm DNA. The medium is changed one day later, and after 2 days, aliquots of the trypsinized cells are placed in wells of a 96 well plate. After five days in culture in the presence of the ligands, the levels of β-galactosidase are measured. The cells are then rinsed and incubated with the substrate, o-nitrophenyl β-D-galactopyranoside. After 16 hours, the plates are read at 405 nm on a plate-reader. Each compound is tested for activity in triplicate at seven different concentrations (10, 2.5, 0.625, 0.156, 0.039, 0.0098, and 0.0024 nM).

5.5. Example 5

Dopamine D$_2$ Receptor Activity

Competition radioreceptor assays are used to determine the affinity (IC$_{50}$'s) of the phenylaminotetralins and other reference ligands for D$_2$ dopamine receptors. D$_2$ assays uses a 90 minute incubation with [$^3$H]YM-09151-2 (0.065 nM) with (+)-butaclamol (0.25 μM) defining nonspecific binding. Jarvie, J. R. et al., *Eur. J. Pharmacol.*, 144:163–171 (1987) and Kula, N. S. et al., *Dev. Brain Res.*, 66:286–287 (1992). Under these conditions, the K$_D$ of [$^3$H]SCH23390 is 0.34 nM and that of [$^3$H]-YM-09151-2 is 0.045 nM. Test agents are evaluated by running, in duplicate, six or more concentrations that bracketed the IC$_{50}$. Three replications are performed, and the resulting data are analyzed using the ALLFIT program.

The binding of the novel radioligand [$^3$H](±)-4 to brain membranes is characterized using assay conditions similar to those developed for the a ligand [$^3$H]DTG. Weber, E. et al., *Proc. Nat. Acad. Sci. U.S.A.*, 83:8784–8788 (1986). Briefly, frozen guinea pig brain (minus cerebellum; obtained from Keystone Biologicals, Cleveland, Ohio) is thawed and homogenized (10 mL/g tissue) in ice-cold 10 mM Tris-HCl buffer containing 0.32 M sucrose, pH 7.0; the homogenate is centrifuged at 1000 g for 15 minutes at 4° C. and the supernatant recentrifuged at 31,000 g for 15 minutes at 4° C. The P$_2$ pellet is suspended in 10 mM Tris buffer (pH 7.4, 25° C.) at 3 mL/g tissue and incubated at room temperature for 15 min at 4° C. The resulting pellet is stored at −70° C. in 10 mM Tris (pH 7.4) at 20 mg protein/mL. To determine binding parameters, a ligand saturation curve is constructed with 1.0 mg of brain protein (50 μL) in glass tubes (triplicate) containing six concentrations (0.02–2.0 nM) of free ligand (F) in 50 mM Tris-HCl buffer, pH 7.4 (2.0 mL total volume), with excess BMY-14802 (5.0 μM) used to define specific binding. Tubes are incubated for 60 minutes at 30° C. and then filtered in a Brandel cell harvester through glass fiber sheets, subsequently cut and counted for tritium by liquid scintillation spectrometry. Results first are plotted in Scatchard-Rosenthal linearized form as ratio of bound/free ligand (B/F) vs. specific binding (B), to provide estimates of apparent affinity K$_D$ (slope) and binding site density B$_{max}$ (x intercept); these values are verified with the LIGAND curve-fitting program adapted to the MacIntosh microcomputer. Munson, P. J. et al., *Analyt. Biochem.*, 107:220–239 (1980). Under these conditions, the K$_D$ of [$^3$H]4 is 0.031 nM. For competitive binding assays, tubes are incubated (60 min, 30° C.) with 50 pM (ca. K$_D$) [3H]4, with 5 μM BMY-14802 used to define nonspecific binding. From 4–8 concentrations (10 pM to 10 μM) of test compounds are used, and the resulting competition data are computer curve-fitted to determine IC$_{50}$±SEM.

5.6. HARD GELATIN CAPSULE DOSAGE FORMS

Table I provides the ingredients of suitable capsule forms of the pharmaceutical compositions of this invention.

TABLE I

| Component | 25 mg capsule | 50 mg capsule | 100 mg capsule |
| --- | --- | --- | --- |
| Ziprasidone Sulfoxide | 25 | 50 | 100 |
| Microcrystalline Cellulose | 90.0 | 90.0 | 90.0 |
| Pre-gelatinized Starch | 100.3 | 97.8 | 82.8 |
| Croscarmellose | 7.0 | 7.0 | 7.0 |
| Magnesium Stearate | 0.2 | 0.2 | 0.2 |

The active ingredient (i.e., ziprasidone sulfoxide) is sieved and blended with the excipients listed. The mixture is filled into suitably sized two-piece hard gelatin capsules using suitable machinery and methods well known in the art. See *Remington's Pharmaceutical Sciences*, 16th or 18th Editions, each incorporated herein in its entirety by reference thereto. Other doses may be prepared by altering the fill weight and, if necessary, by changing the capsule size to suit. Any of the stable hard gelatin capsule formulations above may be formed.

5.7. HARD GELATIN CAPSULE DOASAGE FORMS

Table II provides the ingredients of suitable capsule forms of the pharmaceutical compositions of this invention.

TABLE II

| Component | 25 mg capsule | 50 mg capsule | 100 mg capsule |
| --- | --- | --- | --- |
| Ziprasidone Sulfone | 25 | 50 | 100 |
| Microcrystalline Cellulose | 90.0 | 90.0 | 90.0 |
| Pre-gelatinized Starch | 100.3 | 97.8 | 82.8 |

TABLE II-continued

| Component | 25 mg capsule | 50 mg capsule | 100 mg capsule |
|---|---|---|---|
| Croscarmellose | 7.0 | 7.0 | 7.0 |
| Magnesium Stearate | 0.2 | 0.2 | 0.2 |

The active ingredient (i.e., ziprasidone sulfone) is sieved and blended with the excipients listed. The mixture is filled into suitably sized two-piece hard gelatin capsules using suitable machinery and methods well known in the art. Other doses may be prepared by altering the fill weight and, if necessary, by changing the capsule size to suit. Any of the stable hard gelatin capsule formulations above may be formed.

5.8. COMPRESSED TABLET DOSAGE FORMS

The ingredients of compressed tablet forms of the pharmaceutical compositions of the invention are provided in Table III.

TABLE III

| Component | 25 mg capsule | 50 mg capsule | 100 mg capsule |
|---|---|---|---|
| Ziprasidone Sulfoxide | 25 | 50 | 100 |
| Microcrystalline Cellulose | 90.0 | 90.0 | 90.0 |
| Pre-gelatinized Starch | 100.3 | 97.8 | 82.8 |
| Croscarmellose | 7.0 | 7.0 | 7.0 |
| Magnesium Stearate | 0.2 | 0.2 | 0.2 |

The active ingredient (i.e., ziprasidone sulfoxide) is sieved through a suitable sieve and blended with the excipients until a uniform blend is formed. The dry blend is screened and blended with the magnesium stearate. The resulting powder blend is then compressed into tablets of desired shape and size. Tablets of other strengths may be prepared by altering the ratio of the active ingredient to the excipient(s) or modifying the table weight.

While the invention has been described with respect to the particular embodiments, it will be apparent to those skilled in the art that various changes and modifications may be made without departing from the spirit and scope of the invention as defined in the claims. Such modifications are also intended to fall within the scope of the appended claims.

What is claimed is:

1. A method of treating or prophylaxis of a disorder ameliorated by the inhibition of serotonin reuptake at 5-HT$_2$ receptors and/or the inhibition of dopamine reuptake at dopamine D$_2$ receptors in a patient which comprises administering to a patient in need of such treatment or prophylaxis a therapeutically effective amount of a ziprasidone metabolite, or a pharmaceutically acceptable salt, solvate, hydrate, or clathrate thereof.

2. The method of claim 1 wherein the disorder is selected from the group consisting of neuroleptic disorders, migraines, acute intermittent porphyria, intractable hiccups, Parkinson's disease and epilepsy.

3. A method of treating or prophylaxis of a neuroleptic disorder in a patient which comprises administering to a patient in need of such treatment or prophylaxis a therapeutically effective amount of a ziprasidone metabolite, or a pharmaceutically acceptable salt, solvate, hydrate, or clathrate thereof.

4. The method of claim 1 or 3 wherein the patient is a human.

5. The method of claim 1 wherein the ziprasidone metabolite is ziprasidone sulfoxide or ziprasidone sulfone.

6. The method of claim 3 wherein the neuroleptic disorder is selected from the group consisting of psychosis, affective disorders, and anxiety.

7. The method of claim 6 wherein the psychosis is selected from the group consisting of schizophrenia, schizoaffective psychosis, hallucinations, paranoia, affective psychosis, alcoholic psychoses, arteriosclerotic psychosis, amnestic psychosis, bipolar psychosis, Cheyne-Stokes psychosis, climacteric psychosis, depressive psychosis, drug psychosis, dysmnesic psychosis, hysterical psychosis, infection-exhaustion psychosis, Korsakoff's psychosis, postinfectious psychosis, postpartum psychosis, posttraumatic psychosis, senile psychosis, situational psychosis, toxic psychosis, traumatic psychosis, and Windigo psychosis.

8. The method of claim 6 wherein the affective disorder is selected from the group consisting of depression, attention deficit disorder, attention deficit disorder with hyperactivity, bipolar conditions and manic conditions.

9. The method of claim 6 wherein the anxiety is selected from the group consisting of anxiety attacks, free-floating anxiety, noetic anxiety, separation anxiety, and situation anxiety.

10. The method of claim 1 or 3 wherein the ziprasidone metabolite is administered parenterally, transdermally, mucosally, nasally, buccally, sublingually, or orally.

11. The method of claim 10 wherein the ziprasidone metabolite is administered orally.

12. The method of claim 11 wherein the ziprasidone metabolite administered orally in a tablet or capsule form.

13. The method of claim 1 or 3 wherein the therapeutically effective amount of ziprasidone metabolite is between about 1 mg and about 1000 mg per day.

14. The method of claim 13 wherein the therapeutically effective amount of ziprasidone metabolite is between about 5 mg to about 500 mg per day.

15. The method of claim 14 wherein therapeutically effective amount of ziprasidone metabolite is between about 10 mg to about 200 mg per day.

16. A method of treating or prophylaxis of a neuroleptic disorder in a patient which comprises administering to a patient in need of such treatment or prophylaxis a therapeutically effective amount of ziprasidone sulfoxide, or a pharmaceutically acceptable salt, solvate, hydrate, or clathrate thereof.

17. The method of claim 16 wherein the neuroleptic disorder is psychosis, an affective disorder, or anxiety.

18. A method of treating or prophylaxis of a neuroleptic disorder in a patient which comprises administering to a patient in need of such treatment or prophylaxis a therapeutically effective amount of ziprasidone sulfone, or a pharmaceutically acceptable salt, solvate, hydrate, or clathrate thereof.

19. The method of claim 18 wherein the neuroleptic disorder is psychosis, an affective disorder, or anxiety.

* * * * *